United States Patent
Herlihy et al.

(10) Patent No.: US 9,845,400 B2
(45) Date of Patent: Dec. 19, 2017

(54) WATER-BASED UV INKJET INK

(71) Applicant: SUN CHEMICAL CORPORATION, Parsippany, NJ (US)

(72) Inventors: Shaun Lawrence Herlihy, Chatham (GB); Brian Rowatt, Maidstone (GB); Derek Illsley, Frome (GB)

(73) Assignee: SUN CHEMICAL CORPORATION, Parsippany, NJ (US)

( * ) Notice: Subject to any disclaimer, the term of this patent is extended or adjusted under 35 U.S.C. 154(b) by 0 days.

(21) Appl. No.: 15/312,493

(22) PCT Filed: May 22, 2015

(86) PCT No.: PCT/US2015/032118
§ 371 (c)(1),
(2) Date: Nov. 18, 2016

(87) PCT Pub. No.: WO2015/183719
PCT Pub. Date: Dec. 3, 2015

(65) Prior Publication Data
US 2017/0107386 A1    Apr. 20, 2017

Related U.S. Application Data

(60) Provisional application No. 62/004,345, filed on May 29, 2014.

(51) Int. Cl.
| | |
|---|---|
| C08F 2/46 | (2006.01) |
| C08F 2/50 | (2006.01) |
| C08G 61/04 | (2006.01) |
| C09D 11/102 | (2014.01) |
| C07D 335/16 | (2006.01) |
| C09D 11/101 | (2014.01) |
| C09D 11/38 | (2014.01) |
| C09D 11/033 | (2014.01) |

(52) U.S. Cl.
CPC .......... *C09D 11/102* (2013.01); *C07D 335/16* (2013.01); *C09D 11/033* (2013.01); *C09D 11/101* (2013.01); *C09D 11/38* (2013.01)

(58) Field of Classification Search
None
See application file for complete search history.

(56) References Cited

U.S. PATENT DOCUMENTS

| | | | |
|---|---|---|---|
| 2002/0198289 A1* | 12/2002 | Gummeson | C09D 11/30 523/400 |
| 2006/0119686 A1 | 6/2006 | Odell et al. | |
| 2006/0132566 A1* | 6/2006 | Desie | C09D 11/101 347/100 |
| 2011/0224324 A1 | 9/2011 | Loccufier et al. | |
| 2013/0176370 A1* | 7/2013 | Loccufier | C08F 2/50 347/102 |

OTHER PUBLICATIONS

Lougnot et al, Water-Soluble Polymerization Initiators Based on the Thioxanthone Structure: A Spectroscopic and Laser PHotolysis Study, 1989, Macromolecules, 22, 1, 108-116.*
Aydin et al, One-Component Biomolecular Photoinitiating Systmes, 2a thioxanthone Acetic Acid Derivatives as Photoinitaitors for Free Radical Polymerization, 2003, 24, 718-723.*
PCT International Search Report issued in PCT/US2015/32118 dated Aug. 5, 2015.
Written Opinion of the International Searching Authority issued in PCT/US2015/32118 dated Aug. 5, 2015.
Lougnot, DJ et al. Water-Soluble Polymerization Initiators Based on the Thioxanthone Structure: A Spectroscopic and Laser Photolysis Study. Macromolecules. 1989. vol. 22, pp. 108-116.
Aydin, M et al. Thioxanthone Acetic Acid Derivatives as Photoinitiators for Free Radical Polymerization. Macromol. Rapid Commun. 2003. vol. 24, pp. 718-723.
PubChem-CID-70401136 Create Date: Dec. 1, 2012 (Dec. 1, 2012), p. 3, Fig.
PubChem-CID-58434159 Create Date: Aug. 19, 2012 (Aug. 19, 2012), p. 3, Fig.
PubChem-CID-16060000 Create Date: May 16, 2007 (May 16, 2007), p. 3, Fig.
Notification Concerning Transmittal of International Preliminary Report on Patentability issued in International Application No. PCT/US2015/32118 dated Dec. 8, 2016.

* cited by examiner

*Primary Examiner* — Jessica E Whiteley
(74) *Attorney, Agent, or Firm* — Charles C. Achkar; Ostrolenk Faber LLP

(57) ABSTRACT

The invention describes the use of a water-based UV curable inkjet printing ink wherein the ink is basic due to the presence of a tertiary amine, allowing the complete dissolution of an acid functional photoinitiator of Formula I or Formula IA (wherein $R^1$, $R^2$, $R^3$, n, q, and y are as defined herein). This combination of photoinitiator and tertiary amine allows the rapid low dosage UV curing of a water-based UV formulation using a UV LED light source.

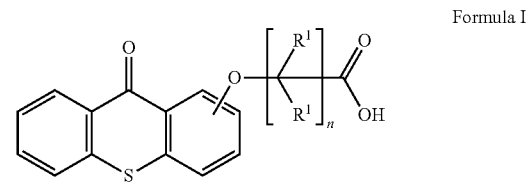

Formula I

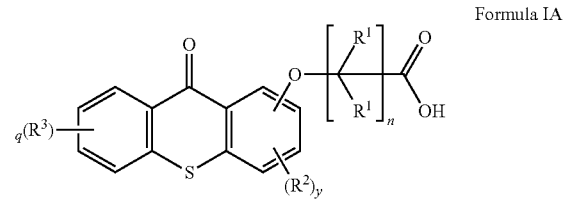

Formula IA

12 Claims, 1 Drawing Sheet

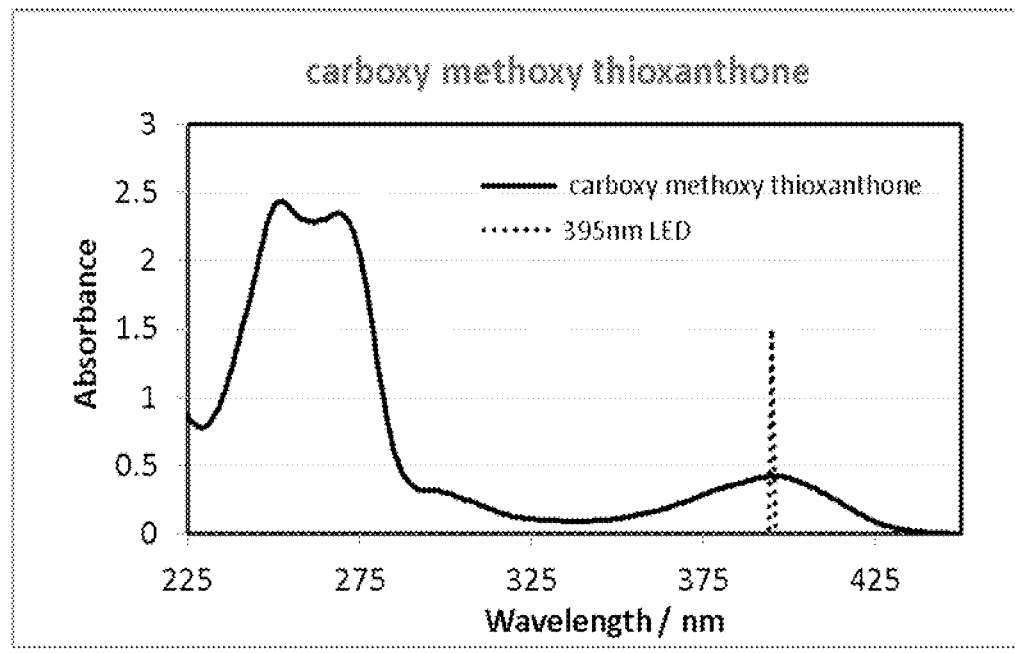

WATER-BASED UV INKJET INK

The present application is a §371 National Phase application based on PCT/US2015/032118 filed May 22, 2016, which claims the benefit of U.S. Provisional Application No. 62/004,345, filed May 29, 2014 the subject matter of each of which is incorporated by reference in their entirety.

FIELD OF THE INVENTION

The present invention is in the field of inks and coating compositions suitable for use in inkjet printing. Compositions of the invention are water-based UV curable inkjet inks that are capable of being cured with a rapid low dosage UV source, such as a UV LED light source.

BACKGROUND

Water-based inkjet inks are well known but are characterized by slow drying and poor resistance qualities in comparison with UV cured inks. However, despite their numerous advantages, UV curable inkjet inks are well known to have problems due to the relatively high film thickness applied (10-12 microns), which causes problems to the printer as a result of an uneven ink build across the web and distortion of the substrate roll in the machine. It is also well known that a potential solution to this problem is the use of a water-based UV curable ink, which initially deposits a similar film thickness to 100% UV inks (10-12 microns), but when the inks have been dried prior to UV curing, the film thickness is reduced to only a few microns and therefore drastically limits this roll distortion, while maintaining many of the positive product resistance properties associated with UV curable inks.

However, both the UV curing process and the removal of water from the printed ink impart a high level of heat to the substrate which can cause shrinkage and distortion that limits the choice of available substrates to the printer.

One strategy to reduce the thermal load to the substrate is to use a UV LED curing lamp in place of a conventional medium pressure mercury arc lamp. However, the choice of suitable photoinitiators which have chromophores extending out to the region where the UV LED lamps emit light is known to be very limited, and this problem becomes further compounded as these compounds tend not to be water soluble in a water-based UV system to the level required to allow adequate curing to take place.

US 2012/0027964 discloses an ink-jet receptive article comprising a substrate having a coating thereon comprising a vinyl lactam polymer or copolymer. The coating is a solvent-based composition comprising a vinyl lactam polymer or copolymer, a solvent, a polymer resin diluent, and optionally a pigment.

WO 2010/029017 discloses the synthesis and use of thioxanthone photoinitiators which are both thioxanthone and acrylate functional. They are described for use in UV curing inkjet inks. EP 0081280 describes an aqueous photo polymerisable composition for the production of a screen printing stencil. The composition contains ethylenically unsaturated monomers which are dispersible, miscible, or soluble in water; tertiary nitrogen-containing compounds; a water-soluble colloid; and a thioxanthone photoinitiator. The exemplified compositions would not be suitable for use in water-based UV inkjet ink. EP 0079119 describes the synthesis and use of water-soluble thioxanthone photoinitiators. The photoinitiators may be used in compositions such as for use in screen stencil production. Green discusses the potential use of carboxymethoxy thioxanthone as a water-soluble photoinitiator (Arthur Green, Octel Chemicals Ltd., Polymers Painting Colour Journal, Oct. 12, 1994, volume 184, number 4358). However, despite these speculations, Irgacure 2959 (from BASF), which is a hydroxyketone photoinitiator, remains the material of choice for water-based UV systems. U.S. Pat. No. 3,966,573 discloses efficient photoinitiator systems based on benzophenone, an amine compound, and a halogenated hydrocarbon.

WO 2005/012448 describes water-based UV curable inkjet compositions based on a plurality of 1,2 and/or 1,3-diol groups along the polymer backbone, and having pendant photo cross-linkable groups attached thereto. WO 02/064689 describes water-based UV curable inkjet inks containing polyurethane diluted in water, a colorant, and a photoinitiator. WO 99/07796 discloses water-based flash UV curable inkjet ink compositions based on a water dispersible or water soluble acrylate polymerisable material with a polymerisable material that is capable of softening the substrate, and is resistant to hydrolysis. U.S. Pat. No. 5,623,001 discloses a UV curable inkjet composition comprising water, a water miscible UV curable polymerisable material, a photoinitiator, and a colorant. EP 2075293 discloses an ink-jet ink comprising water, a pigment dispersion, water-soluble polymerizing or cross-linking substance having an ethylenically unsaturated group, and a water-soluble photoinitiator. U.S. Pat. No. 8,071,665 discloses a single phase aqueous composition that is suitable for inkjet printing. The composition comprises a mixture of curable materials including at least two curable oligomers, and one or more co-solvents for the curable materials. The curable materials are fully in solution. EP 1469049 teaches that the open time of a UV curable water-based inkjet ink may be improved through the use of a water-soluble UV monomer as a humectant.

GB 2256874 discloses a photocurable composition comprising a water dilutable multifunctional polyurethane acrylate oligomer, a multifunctional acrylate monomer, water, and a vinyl ether monomer. The compositions are useful as screen printing inks. US 2002/0065335 describes an aqueous photocurable composition comprising at least water, a polymerisable material, and a water-soluble photopolymerisation initiator. The application covers only cleavage type photoinitiators. EP 2703459 and EP 2703 458 disclose a photocurable ink composition containing colorant, water, photo-initiator, UV curable polyurethane dispersions, hydrophobic radiation-curable monomers and water-soluble or water-miscible radiation curable monomers. A printing method is also disclosed. US 2012/0225968 teaches the use of a urethane acrylate oligomer for use in solvent- and water-based inks. The ink compositions contain, in addition to the urethane acrylate, a compound having radical polymerizable groups and a photoradical polymerization initiator. US 2002/0121631 teaches UV curable overprint varnishes that can be applied in-line over conventional lithographic inks. The use of benzophenone and an amine synergist is shown to be an effective combination of photoinitiators. U.S. Pat. No. 5,395,863 discloses UV cured screen inks. The UV curable compositions include a free radically polymerizable monomer or prepolymer, and a different monomer containing an N-vinyl group. The compositions include a photoinitiator when they are to be cured by exposure to UV light, and can also include a photo accelerator.

Up to now, most attempts to develop improved water-based UV curable ink and coating compositions use either Irgacure 2959 as a photoinitiator (solubility in water 1.0%), look to develop more water soluble photoinitiators, particularly cleavage type, or use standard photoinitiators in an emulsion water-based UV system.

What is clear is that currently, there is no suitable approach to formulating a water-based UV inkjet ink that can be cured using a UV LED lamp.

SUMMARY OF THE INVENTION

The present invention provides water-based inkjet inks that are curable using low dosage UV LED light. The ink is basic due to the presence of a tertiary amine, allowing the complete dissolution of an acid functional photoinitiator according to Formula I and IA below. The combination of photoinitiator and tertiary amine allows the rapid low dosage UV curing of the water-based UV formulation using a UV LED light source.

In a certain aspect, the present invention provides an alkaline energy curable water-based inkjet ink or coating composition comprising:

a) a photoinitiator of Formula I:

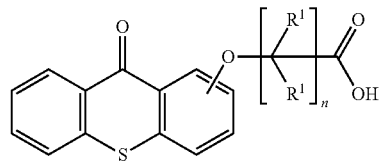

Formula I wherein each $R^1$ is an independently selected hydrogen or a $C_1$-$C_4$ alkyl group; and n is a number from 0 to 8;
b) a polymer which is water-soluble, or dispersible in water, either as a liquid in liquid emulsion, or a particle suspension;
c) water; and
d) one or more tertiary amine synergists;
wherein the pH of the composition is between about 7.0 and about 9.5.

In a particular aspect, the present invention provides an alkaline energy curable water-based inkjet ink or coating composition comprising:

a) a photoinitiator of Formula IA:

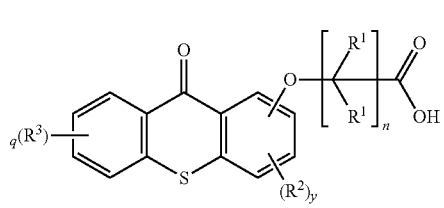

Formula IA wherein each $R^1$ is an independently selected hydrogen or a $C_1$-$C_4$ alkyl group;
each $R^2$ and $R^3$ is independently selected from the group consisting of hydrogen, $C_1$-$C_4$ alkyl, $C_1$-$C_4$ alkoxy, and halogen;
y is 0 or 1;
q is 0, 1, or 2;
and n is a number from 0 to 8;
b) a polymer which is water-soluble, or dispersible in water, either as a liquid in liquid emulsion, or a particle suspension;
c) water; and
d) one or more tertiary amine synergists;
wherein the pH of the composition is between about 7.0 and about 9.5.

The water-based inkjet inks can be cured using any UV energy source, including, but not limited to, mercury arc lamps and LED light sources. Preferably, the inks are suitable for curing by LED light source.

Advantageously, the ratio of the amine to the compound of Formula I or IA is greater than 1:1. For example, the ratio of amine:compound of Formula I or IA can be greater than 2:1; or greater than 5:1; or greater than about 20:1.

The thioxanthone photoinitiator CMTX absorbs light principally in the region around 395 nm and is perfectly suited to use with UV LED curing lamps (see FIG. 1). The UV absorbance spectrum of carboxymethoxy thioxanthone exhibited in FIG. 1 shows that this material has a strong absorbance band centered at 395 nm and is therefore perfectly positioned to efficiently absorb the UV light emitted at 395 nm from a typical commercial LED curing lamp (also shown). The subsequent excited state of carboxymethoxy thioxanthone then undergoes a bimolecular reaction with a tertiary amine synergist to generate free radicals capable of initiating the curing reaction. The free acid CMTX is almost completely insoluble in both "conventional" 100% solids UV curing systems and in water. It is only the inclusion of an amine, such as triethanolamine, that renders it soluble in a water-based environment, and simultaneously acts as an amine synergist that works effectively with the CMTX to initiate effective curing in both medium pressure mercury arc lamp and UV LED lamp curing situations.

BRIEF DESCRIPTION OF THE DRAWINGS

FIG. 1: FIG. 1 shows the UV spectral absorbance of carboxymethoxy thioxanthone and the emission spectrum of a 395 nm LED lamp. The UV spectrum of carboxymethoxy thioxanthone was acquired at a concentration of 20.4 mg/liter in methanol using the Lambda 650 UV visible spectrometer, scanning from 225 to 450 nm.

DETAILED DESCRIPTION OF THE INVENTION

It is to be understood that the foregoing general description and the following detailed description are exemplary and explanatory only, and are not restrictive of any subject matter claimed.

Unless otherwise defined, all technical and scientific terms used herein have the same meaning as is commonly understood by one of skill in the art to which the inventions belong. All patents, patent applications, published applications and publications, websites and other published materials referred to throughout the entire disclosure herein, unless noted otherwise, are incorporated by reference in their entirety for any purpose.

Definitions

In this application, the use of the singular includes the plural unless specifically stated otherwise. As used herein, the singular forms "a," "an" and "the" are intended to include the plural forms as well, unless the context clearly indicates otherwise.

In this application, the use of "or" means "and/or" unless stated otherwise.

As used herein, the terms "comprises" and/or "comprising" specify the presence of the stated features, integers, steps, operations, elements, and/or components, but do not preclude the presence or addition of one or more other features, integers, steps, operations, elements, components, and/or groups thereof. Furthermore, to the extent that the terms "includes," "having," "has," "with," "composed," "comprised" or variants thereof are used in either the detailed description or the claims, such terms are intended to be inclusive in a manner similar to the term "comprising."

As used herein, ranges and amounts can be expressed as "about" a particular value or range. "About" is intended to also include the exact amount. Hence "about 5 percent" means "about 5 percent" and also "5 percent." "About" means within typical experimental error for the application or purpose intended.

As used herein, the terms "(meth)acrylate" or "(meth)acrylic acid" include both acrylate and methacrylate compounds.

Throughout this disclosure, all parts and percentages are by weight (wt % or mass % based on the total weight) and all temperatures are in ° C. unless otherwise indicated.

As used herein, the term "alkyl" refers to straight chain and branched saturated non-cyclic hydrocarbons, having from 1 to 4 carbon atoms. Representative straight chain alkyl groups include methyl, -ethyl, -n-propyl, and -n-butyl, and the like.

As used herein, the term "alkoxy" means a straight chain or branched non-cyclic hydrocarbon having one or more ether groups and from 1 to 4 carbon atoms. Representative straight chain and branched alkoxys include -methoxy, -ethoxy, -propoxy, -butyloxy, and the like.

As used herein, the term "halogen" refers to chloro, fluoro, bromo, or iodo.

Inkjet Inks

What we have found, surprisingly, is that photoinitiators according to Formula I and Formula IA (below), and particularly 2-carboxymethoxy thioxanthone, are readily soluble in alkaline water-based UV formulations and are capable of being used without fear of settlement or re-crystallisation at levels that enable rapid UV curing to take place using a UV LED light source. Typically, compounds of this type are poorly soluble, and tend to precipitate out, causing problems with the performance of the ink. What is of further surprise is that the level of performance from such formulations using a UV LED light source is at its highest at relatively low CMTX levels and higher amine levels than would be predicted based on conventional formulating wisdom from those skilled in the art. Based on the teaching of the prior art, one of skill in the art would expect that a ratio of about 1:1 of CMTX:amine would be optimal, and that increasing the level of amine compared to the amount of CMTX would be detrimental to the performance of the ink or coating. The carboxylic acid group (in Formula I and Formula IA) is critical in this respect as it also balances the tendency towards alkaline pH resulting from incorporation of an amine synergist.

In a particular aspect, the present invention provides an alkaline energy curable water-based inkjet ink or coating composition comprising:

a) a photoinitiator of Formula I:

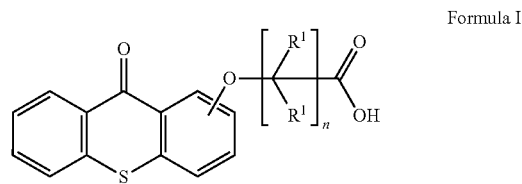

Formula I wherein each $R^1$ is an independently selected hydrogen or a $C_1$-$C_4$ alkyl group; and n is a number from 0 to 8;

b) a polymer which is water-soluble, or dispersible in water, either as a liquid in liquid emulsion, or a particle suspension;

c) water; and d) one or more tertiary amine synergists;

wherein the pH of the composition is between about 7.0 and about 9.5.

In a particular aspect, the present invention provides an alkaline energy curable water-based inkjet ink or coating composition comprising:

a) a photoinitiator of Formula IA:

Formula IA wherein each $R^1$ is an independently selected hydrogen or a $C_1$-$C_4$ alkyl group;

each $R^2$ and $R^3$ is independently selected from the group consisting of hydrogen, $C_1$-$C_4$ alkyl, $C_1$-$C_4$ alkoxy, and halogen;

y is 0 or 1;

q is 0, 1, or 2;

and n is a number from 0 to 8;

b) a polymer which is water-soluble, or dispersible in water, either as a liquid in liquid emulsion, or a particle suspension;

c) water; and d) one or more tertiary amine synergists;

wherein the pH of the composition is between about 7.0 and about 9.5.

The inks can also contain other additives normally used in ink and coating compositions. For example, the inks could contain one or more water compatible solvents, one or more water soluble monomers, and one or more additional photoinitiators.

The water-based energy curable inks generally contain about 0.1 to about 5 wt % of a photoinitiator of Formula I or IA. Preferably, the photoinitiator of Formula I or IA is present in an amount of about 0.1 to about 2 wt %. Photoinitiators of Formula I or IA include, but are not limited to, 2-[carboxymethoxy]thioxanthone, 2-[2-ethyl (carboxymethoxy)]thioxanthone, 2-[2-methyl(carboxymethoxy)]thioxanthone, and 2-[carboxy-n-pentyl-5-oxy]thioxanthone.

The polymer which is water-soluble, or dispersible in water either as a liquid in liquid emulsion or particle suspension, is present in an amount of about 15-35% of a water dispersion containing about 40% solids. For example, the polymer could be present in an amount of about 15 to 30 wt %; 20 to 30 wt %; or 20 to 25 wt %.

The water-based energy curable ink can contain one or more water compatible solvents in an amount of from about 0 to 40 wt %. For example, the one or more water compatible solvents may be present in an amount of about 1 to 35 wt %; about 5 to 30 wt %; about 10 to 25 wt %; or about 15 to 20 wt %. Preferably, the inks contain about 1 to 30 wt % water compatible solvents.

Advantageously, the water-based energy curable inks contain about 20 to 80 wt % of water. For examples, the inks may contain about 20 to 75 wt %; about 25 to 70 wt %; about 30 to 70 wt %; or about 25 to 70 wt % water. Preferably, the inks contain about 30 to about 70 wt % water.

The water-based energy curable inks may also contain one or more water compatible solvents. These solvents can be present in an amount from about 0 to about 40 wt %. For example, the solvents can be present in an amount of from about 1 to about 35 wt %; from about 2 to about 30 wt %; from about 5 to about 30 wt %; from about 10 to about 25 wt %; or from about 10 to about 20 wt %.

The water-based energy curable inks may also contain one or more water soluble monomers. The water soluble monomers may be present in an amount of from about 0 to about 15 wt %. For example, the water soluble monomers may be present in an amount of from about 1 to about 10 wt %; from about 1 to about 5 wt %; or from about 2 to about 5 wt %.

Advantageously, the one or more tertiary amine synergists are present in an amount of from about 0.1 to about 4 wt %. For example, the tertiary amine synergists may be present in an amount of from about 0.1 to 3.5 wt %; from about 0.1 to about 3 wt %; or from about 1 to about 3 wt %.

The water-based energy curable inks may also contain one or more additional photoinitiators. The additional photoinitiators may be present in an amount of from about 0 to about 2 wt %. For example, the additional photoinitiators may be present in an amount of from about 0.1 to 2 wt %; from about 0.1 to about 1.5 wt %; or from about 0.5 to about 1 wt %.

Advantageously, the ratio of amine to the Formula 1 or Formula IA photoinitiator is greater than 1:1. Preferably, the ratio of amine to the Formula 1 or Formula IA photoinitiator is greater than 1.5:1; or greater than 2:1; or greater than 5:1; or greater than 10:1; or greater than 15:1; or greater than 20:1.

The water-based energy curable inkjet inks are generally alkaline. Preferably, the pH of the ink is greater than or equal to about 7.0. Preferably, the pH of the ink is less than or equal to about 9.5. For example, the pH of the ink can be between 7.0 and 9.5. For example, the pH of the ink can be 7.0, 7.5, 8.0, 8.5, 9.0, or 9.5.

Advantageously, the present invention provides a printed article comprising the alkaline energy curable water-based inkjet ink or coating composition. The substrate of which the printed article is made is not restricted. Any substrate that is suitable for inkjet printing can be used. For example, the substrate may be paper, paperboard, polymer films, plastic, metal, etc.

It is further suggested that the thermal load on the substrate can be reduced to an even greater extent if the use of a near Infrared (NIR) drying lamp (such as described in US20090120361) is employed in combination with a UV LED curing lamp.

The present invention describes the use of a water-based UV curable inkjet printing ink wherein the ink is basic due to the presence of a tertiary amine, allowing the complete dissolution of an acid functional photoinitiator (Formula I or Formula IA), and preferably the compound 2-carboxymethoxy thioxanthone. This combination of photoinitiator and tertiary amine allows the rapid low dosage UV curing of a water-based UV formulation using a UV LED light source.

It is understood that the inks of the present formulation could contain a wide range of raw materials that are compatible with either or both energy curable and water-based ink systems. These materials include, but are not limited to, polymers and resins, monomers, oligomers, solvents, colorants, photoinitiators, amine synergists, surface control additives, defoamers, biocides, etc.

The ink formulations are typically based on the use of acrylated polyurethane dispersions such as those supplied as MS 10/1312, and MS 10/1311 (from Allnex); Neorad R-440, R-441, R-444, R-447, R-448, R-465, UV-14, UV-20, UV-65, and UV-TN6711 (from DSM); Laromer LR8949, LR8983, LR9005, UA 9059, UA9060, UA9064, and UA9095 (from BASF); and Bayhydrol UV 2282, UV 2317, UV VP LS 2280, UV VP LS 2317, UV XP 2629, UV XP 2687, UV XP 2689, UV XP 2690, and UV XP 2775 (from Bayer).

It is also possible for a skilled formulator to create similarly functional products based on the use of other acrylate and non-functional resin technologies. Possibilities in this area would include acrylated polyester dispersions such as the Laromer PE range from BASF; water soluble epoxy acrylates such as Laromer 8765 from BASF and CN132 from Sartomer; styrene maleic anhydride adducts (SMA) where the anhydride group of a styrene-maleic copolymer is reacted with a OH-functional monomer; acetoacetate-functional polymers such as acetoacetate-functional poly(vinyl alcohol) such as Gohsenx Z from Nippon Gohsei; acrylic emulsions such as those sold under the trade names Joncryl (BASF), Revacryl (Synthomer), Hycar (Lubrizol), Neocryl (DSM), Neboplast (Necarbo), and the Picassian AC range (Picassian Polymers); solution acrylics such as those sold under the trade names Joncryl (BASF); poly(meth)acrylic acid such as those sold under the trade name Sokalan (BASF); polyurethane dispersions such as those sold under the trade names Sancure (Lubrizol), Syntegra (Dow), Luplen (BASF), and Beetafin (BIP); polyester emulsions such as those sold under the trade names Eastek (Eastman); PVC Emulsions such as those sold under the trade names Vycar (Lubrizol); polyamide dispersions such as those sold under the trade names Casamid (Thomas Swann) and Hydrosize (Michelman); water-based alkyds such as those sold under the trade names Synaqua (Arkema); poly(vinyl alcohol) such as those sold by Kuraray, Nippon Gohsei & Celanese; polyethylene glycols; poly(vinyl pyrrolidones such as those sold under the trade names PVP-K15, K30, K60, K90 (ISP); maleic resins such as those sold under the trade names Hydrorez (Lawter); and natural resins such as water-based shellacs (Worlee), Procote (DOW), and Revertex (Synthomer).

These various resin types may, where applicable, be neutralized using organic bases, including, but not limited to, ammonia, triethanolamine, triisopropanolamine, dimethyl aminoethanol or arginine. Alternatively, they may be neutralised by an inorganic base including but not limited to alkali metal oxides, alkali metal hydroxides or alkali metal carbonates, with sodium hydroxide or potassium hydroxide being the preferred inorganic bases. Where tertiary amines such as triethanolamine are used as neutralising agents, they will serve a dual function as both neutralising agent, aiding the solubility of the photoinitiator, and as an amine synergist actively involved in the production of free radicals with the photoinitiator. If desired, it would also be possible to use an inorganic base as an additional component in the composition to aid the solubility of the thioxanthone photoinitiator, although this would not be the preferred approach.

A partial list of some of the meth(acrylate) monomers that could be used to formulate the inks of the present invention is included below. This includes both materials that are fully water soluble and therefore easy to use, such as polyethylene glycol 400 diacrylate, and materials which would be classed as insoluble or have limited water compatibility, but are capable of being used by those with good formulating expertise, possibly co-solvents to aid compatibility.

Examples of suitable monofunctional ethylenically unsaturated monomers include, but are not limited to, the following, where the term ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts. Suitable compounds include, but are not limited to, isobutyl acrylate; cyclohexyl acrylate; iso-octyl acrylate; n-octyl acrylate; isodecyl acrylate; iso-nonyl acrylate; octyl/decyl acrylate; lauryl acrylate; 2-propyl heptyl acrylate; tridecyl acrylate; hexadecyl acylate; stearyl acrylate; iso-stearyl acrylate; behenyl acrylate; tetrahydrofurfuryl acrylate; 4-t.butyl cyclohexyl acrylate; 3,3,5-trimethylcyclohexane acrylate; isobornyl acrylate; dicyclopentyl acrylate; dihydrodicyclopentadienyl acrylate; dicyclopentenyloxyethyl acrylate; dicyclopentanyl acrylate; benzyl acrylate; phenoxyethyl acrylate; 2-hydroxy-3-phenoxypropyl acrylate; alkoxylated nonylphenol acrylate; cumyl phenoxyethyl acrylate; cyclic trimethylolpropane formal acrylate; 2(2-ethoxyethoxy) ethyl acrylate; polyethylene glycol monoacrylate; polypropylene glycol monoacrylate; caprolactone acrylate; ethoxylated methoxy polyethylene glycol acrylate; methoxy triethylene glycol acrylate; tripropyleneglycol monomethyl ether acrylate; diethylenglycol butyl ether acrylate; alkoxylated tetrahydrofurfuryl acrylate; ethoxylated ethyl hexyl acrylate; alkoxylated phenol acrylate; ethoxylated phenol acrylate; ethoxylated nonyl phenol acrylate; propoxylated nonyl phenol acylate; polyethylene glycol o-phenyl phenyl ether acrylate; ethoxylated p-cumyl phenol acrylate; ethoxylated nonyl phenol acrylate; alkoxylated lauryl acrylate; ethoxylated tristyrylphenol acrylate; N-(acryloyloxyethyl)hexahydrophthalimide; N-butyl 1,2 (acryloyloxy) ethyl carbamate; acryloyl oxyethyl hydrogen succinate; octoxypolyethylene glycol acrylate; octafluoropentyl acrylate; 2-isocyanato ethyl acrylate; acetoacetoxy ethyl acrylate; 2-methoxyethyl acrylate; dimethyl aminoethyl acrylate; 2-carboxyethyl acrylate; 4-hydroxy butyl acrylate; combinations thereof; and the like.

Examples of suitable multifunctional ethylenically unsaturated monomers include but are not limited to the following, where the term ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts. Suitable compounds include, but are not limited to, 1,3-butylene glycol diacrylate; 1,4-butanediol diacrylate; neopentyl glycol diacrylate; ethoxylated neopentyl glycol diacrylate; propoxylated neopentyl glycol diacrylate; 2-methyl-1,3-propanediyl ethoxy acrylate; 2-methyl-1,3-propanediol diacrylate; ethoxylated 2-methyl-1,3-propanediol diacrylate; 3 methyl 1,5-pentanediol diacrylate; 2-butyl-2-ethyl-1,3-propanediol diacrylate; 1,6-hexanediol diacrylate; alkoxylated hexanediol diacrylate; ethoxylated hexanediol diacrylate; propoxylated hexanediol diacrylate; 1,9-nonanediol diacrylate; 1,10 decanediol diacrylate; ethoxylated hexanediol diacrylate; alkoxylated hexanediol diacrylate; diethyleneglycol diacrylate; triethylene glycol diacrylate; tetraethylene glycol diacrylate; polyethylene glycol diacrylate; propoxylated ethylene glycol diacrylate; dipropylene glycol diacrylate; tripropyleneglycol diacrylate; polypropylene glycol diacrylate; poly (tetramethylene glycol) diacrylate; cyclohexane dimethanol diacrylate; ethoxylated cyclohexane dimethanol diacrylate; alkoxylated cyclohexane dimethanol diacrylate; polybutadiene diacrylate; hydroxypivalyl hydroxypivalate diacrylate; tricyclodecanedimethanol diacrylate; 1,4-butanediylbis[oxy(2-hydroxy-3,1-propanediyl)]diacrylate; ethoxylated bisphenol A diacrylate; propoxylated bisphenol A diacrylate; propoxylated ethoxylated bisphenol A diacrylate; ethoxylated bisphenol F diacrylate; 2-(2-Vinyloxyethoxy)ethyl acrylate; dioxane glycol diacrylate; ethoxylated glycerol triacrylate; glycerol propoxylate triacrylate; pentaerythritol triacrylate; trimethylolpropane triacrylate; caprolactone modified trimethylol propane triacrylate; ethoxylated trimethylolpropane triacrylate; propoxylated trimethylol propane triacrylate; tris (2-hydroxy ethyl) isocyanurate triacrylate; e-caprolactone modified tris (2-hydroxy ethyl) isocyanurate triacrylate; melamine acrylate oligomer; pentaerythritol tetraacrylate; ethoxylated pentaerythritol tetraacrylate; di-trimethylolpropane tetra acrylate; dipentaerythritol pentaaacrylate; dipentaerythritol hexaaacrylate; ethoxylated dipentaerythritol hexaacrylate; combinations thereof; and the like.

Other functional monomer classes capable of being used in part in these formulations at a level between 0 and 40 percent by mass according to the entire ink composition include cyclic lactam such as N-vinyl caprolactam, N-vinyl oxazolidinone and N-vinyl pyrrolidone, and secondary or tertiary acrylamides such as acryloyl morpholine, diacetone acrylamide, N-methyl acrylamide, N-ethyl acrylamide N-isopropyl acrylamide, N-t-butyl acrylamide, N-hexyl acrylamide, N-cyclohexyl acrylamide, N-octyl acrylamide, N-t-octyl acrylamide, N-dodecyl acrylamide, N-benzyl acrylamide, N-(hydroxymethyl)acrylamide, N-isobutoxymethyl acrylamide, N-butoxymethyl acrylamide, N,N-dimethyl acrylamide, N,N-diethyl acrylamide, N,N-propyl acrylamide, N,N-dibutyl acrylamide, N,N-dihexyl acrylamide, N,N-dimethylamino methyl acrylamide, N,N-dimethylamino ethyl acrylamide, N,N-dimethylamino propyl acrylamide, N,N-dimethylamino hexyl acrylamide, N,N-diethylamino methyl acrylamide, N,N-diethylamino ethyl acrylamide, N,N-diethylamino propyl acrylamide, N,N-dimethylamino hexyl acrylamide, and N,N'-methylenebisacrylamide, and the like. Of these, diacetone acrylamide is particularly preferred.

The ink composition according to the present invention includes water. This would preferably not contain ionic impurities and is therefore preferably ion exchanged or distilled water. The quantity of water used according to the present invention, including that which is supplied as part of raw materials used, is preferably 20 to 80%, more preferably 30 to 70% by mass according to the entire ink composition.

The ink may also contain one or more water-compatible organic solvents, preferably at a level of between 1 and 40%, more preferably 1 to 30% by mass according to the entire ink composition, which have a primary function as a humectant, preventing drying of the ink in the inkjet heads and thus preventing them from clogging, and a secondary function as a wetting aid, allowing the inkjet drops to spread on the substrate. Examples of suitable solvents would include materials which are not highly flammable or volatile, typically an alkylene glycol ether or ether acetate type, with the following non-limiting examples: 4-hydroxy-4-methyl-2-pentanone, diethylene glycol butyl ether, diethylene glycol ethyl ether, diethylene glycol methyl ether, diethylene glycol monoethyl ether acetate, diethylene glycol monopropyl ether, dipropylene glycol ethyl ether, dipropylene glycol methyl ether, ethylene glycol butyl ether, ethylene glycol ethyl ether, ethylene glycol isopropyl ether, ethylene glycol methyl ether, ethylene glycol propyl ether, glycerine carbonate, N-methyl 2-pyrrolidone, propylene glycol, propylene glycol ethyl ether, propylene glycol ethyl ether acetate, propylene glycol methyl ether, propylene glycol n-propyl ether, triethylene glycol butyl ether, triethylene glycol methyl ether, tripropylene glycol, tripropylene glycol methyl ether, and the like.

Suitable photoinitiators which can be used in combination with the thioxanthone photoinitiator of the present invention include, but are not limited to, those which are capable of absorbing UV light in the region where LED light sources emit. Typically this is 405 nm, 395 nm, 385 nm, 375 nm and 365 nm, although other LED's with lower wavelength emissions have been described. Such photoinitiators are typically not water soluble, and therefore relatively difficult to use at any significant level. These additional photoinitiators would preferably be acyl phosphine oxides, including but not limited to, 2,4,6-trimethylbenzoyl-diphenylphosphine oxide; 2,4,6-trimethylbenzoyl-diphenyl phosphinate; bis(2,4,6-trimethylbenzoyl)-phenylphosphine oxide; and the like. Other possible photoinitiators include non-acid functional thioxanthone photoinitiators such as 2-4-diethylthioxanthone, isopropylthioxanthone, 2-chlorothioxanthone, 1-chloro-4-propoxythioxanthone, GENOPOL TX1 from Rahn, OMNIPOL TX from IGM or SPEEDCURE 7010 from Lambson; bis dialkylamino benzophenones such as 4 4,4-bis(diethylamino)benzophenone; anthraquinones such as 2-ethyl anthraquinone; and the like.

It is also possible to use certain photoinitiators such as α-aminoketones, which are well known to undergo triplet energy transfer processes with certain thioxanthones, and which can be included as useful, even though they may not themselves have any significant light absorption at the LED emission wavelength. Examples include, but are not limited to, 2-methyl-1-[4-(methylthio)phenyl]-2-morpholinopropan-1-one; 2-benzyl-2-dimethylamino-1-(4-morpholino-phenyl)-butanone-1; 2-dimethylamino-2-(4-methyl-benzyl)-1-(4-morpholin-4-yl-phenyl)-butan-1-one; and Omnirad 910 from IGM resins; and the like.

An amine synergist may also be included in the ink formulation. Suitable examples include, but are not limited to, the following: aliphatic alkanolamines such as triethanolamine, N-methyl ethanolamine and N,N-dimethyl ethanolamine; and aminoacrylates such as EBECRYL 80/81/83/85/880/841/7100/P116, and EBECRYL LEO 10551/10552/10553, available from Allnex; CN 501/550/3705/3715/3735/3755/381/386 and UVA421, all available from Sartomer; Photomer 4967/4775/4969/5006/5662/5930/5960, all available from IGM Resins; GENOMER 5142, 5161, 5171 and 5275 from Rahn; LAROMER LR8996, LR8997, LR8869, LR8889, PO 83F, PO 84F and PO 94F all available from BASF; combinations thereof, and the like. Aromatic aminobenzoate esters are also possible, but less desirable than alkanolamines and aminoacrylates, because of their lower water solubility. Examples include ethyl-4-(dimethylamino)benzoate, 2-ethylhexyl-4-(dimethylamino) benzoate, 2-(dimethylamino)ethylbenzoate, and polymeric aminobenzoates such as OMNIPOL ASA from IGM Resins, GENOPOL AB1/AB2 from Rahn, and SPEEDCURE 7040 from Lambson, combinations thereof, and the like. The use of compounds with both tertiary amine and acidic functionalities is also possible, and useful in regulating the pH of the composition, while still keeping optimum levels of amine synergist present for efficient reaction with the thioxanthone photoinitiator. Such compounds include isomers of N,N-dialkylaminobenzoic acids, N,N-dimethylglycine, and isomers of N,N-dialkylaniline sulphonic acids. Of these, 4-(dimethylamino)benzoic acid is particularly preferred.

Since the inks of the current invention are primarily water-based in nature, it is also preferable to include a biocide or anti-mold agent. Suitable examples include products based on the following biocide structural types: benzisothiazolinone, bromo-nitro-propane-diol, isothiazolinone, ethylenedioxydimethanol, or iodo-propynyl butyl carbamate, which are marketed under the trade names Intercide (Akcros Chemicals) or Nipacide (Clariant). Other types of biocide that could be considered include sodium dehydroacetate (Geogard 111S from Lonza), sodium benzoate (Vancide 51 from R. T. Vanderbilt), sodium pyridinethiol-1-oxide (Sodium Omadine from Arch Chemicals), sodium salt of o-phenylphenol (Dowicide A from DOW Chemical) and ethyl p-hydroxybenzoate (Nipastat Sodium from Aako). These are preferably used at an amount of 0.01 to 1.00% by mass in the ink composition.

Defoamers can also optionally be included in the formulation; these prevent the formation of foam during manufacture of the ink and also while jetting. Defoamers are particularly important with recirculating printheads. Examples of suitable defoamers include TEGO FOAMEX N, FOAMEX 1488, 1495, 3062, 7447, 800, 8030, 805, 8050, 810, 815N, 822, 825, 830, 831, 835, 840, 842, 843, 845, 855, 860, and 883, TEGO FOAMEX K3, TEGO FOAMEX K7/K8 and TEGO TWIN 4000 available from Evonik. Available from BYK are BYK-066N, 088, 055, 057, 1790, 020, BYK-A 530, 067A, and BYK 354. The additives DC62, DC65, DC 68, DC71 and DC74 are available from Dow Corning. Agitan 120, 150, 160, 271, 290, 298, 299, 350, 351, 731, 760, 761, and 777 are available from Munzing. Surfynol 104PA, AD01, DF-110, DF-58, DF-62, DF-66, DF-695, DF-70, and MD-20 are available from Air Products.

Surface control additives are often optionally used to control the surface tension of the ink, which is required to adjust the wetting on the face plate of the printhead, and also to give the desired drop spread on the substrate, or, in the case of multi pass inkjet printing, wet on dry drop spread. They can also be used to control the level of slip and scratch resistance of the coating. Examples of suitable surface control additives include but are not limited to TEGO FLOW 300, 370, and 425, TEGO GLIDE 100, 110, 130, 406, 410, 411, 415, 420, 432, 435, 440, 482, A115, and B1484, TEGO GLIDE ZG 400, TEGO RAD 2010, 2011, 2100, 2200N, 2250, 2300, 2500, 2600, 2650, and 2700, TEGO TWIN 4000 and 4100, TEGO WET 240, 250, 260, 265, 270, 280, 500, 505, and 510 and TEGO WET KL245, all available from Evonik. Available from BYK are BYK 333 and 337, BYK UV 3500, BYK 378, 347 and 361, BYK UV 3530 and 3570, CERAFLOUR 998 and 996, NANOBYK 3601, 3610, and 3650, and CERMAT 258. Available from Cytec are EBECRYL 350 and 1360, MODAFLOW 9200, and EBECRYL 341. From Sartomer the aliphatic silicone acrylate CN9800 may be used. Surfynol 104, 420, 440, 465, 485, 61, 82, and 2502 are available from Air Products. Multiwet BD, EF, SU, SO, and VE are available from Croda. Capstone FS-30, 31, 34, 35, 50, 51, 60, 61, 63, 64, 65, and 3100 are available from Du Pont.

Included in the ink formulation can optionally be a suitable de-aerator. These prevent the formation of air inclusions and pinholes in the cured coating. These also reduce rectified diffusion, which can cause reliability issues in the printhead. Examples include the following products available from Evonik: TEGO AIREX 900, 910, 916, 920, 931, 936, 940, 944, 945, 950, 962, 980, and 986.

The ink compositions of the present invention may optionally contain one or more colorants, including pigments and/or dyes. Examples of suitable organic or inorganic pigments include carbon black, zinc oxide, titanium dioxide, phthalocyanine, anthraquinones, perylenes, carbazoles, monoazo and disazobenzimidazoles, rhodamines, indigoids, quinacridones, diazopyranthrones, dinitroanilines, pyrazoles, diazopyranthrones, pyrazoles, dianisidines, pyranthrones, tetracholoroisoindolines, dioxazines, monoazoacrylides and anthrapyrimidines. The dyes include but are not limited to azo dyes, anthraquinone dyes, xanthene dyes, azine dyes, combinations thereof and the like.

Commercial organic pigments classified according to Color Index International may be used, including, but not limited to, those according to the following trade designations: blue pigments PB1, PB15, PB15:1, PB15:2, PB15:3, PB15:4, PB15:6, PB16, PB60; brown pigments PBS, PB23, and PB265; green pigments PG1, PG7, PG10 and PG36; yellow pigments PY3, PY14, PY16, PY17, PY24, PY65, PY73, PY74 PY83, PY95, PY97, PY108, PY109, PY110, PY113, PY128, PY129, PY138, PY139, PY150, PY151, PY154, PY156, PY175, PY180 and PY213; orange pigments PO5, PO15, PO16, PO31, PO34, PO36, PO43, PO48, PO51, PO60, PO61 and PO71; red pigments PR4, PR5, PR7, PR9, PR22, PR23, PR48, PR48:2, PR49, PR112, PR122, PR123, PR149, PR166, PR168, PR170, PR177, PR179, PR190, PR202, PR206, PR207, PR224 and PR254: violet pigments PV19, PV23, PV32, PV37 and PV42; black pigments PBk1, PBk6, PBk7, PBk8, PBk9, PBk10, PBk11, PBk12, PBk13, PBk14, PBk17, PBk18, PBk19, PBk22, PBk23, PBk24, PBk25, PBk26, PBk27, PBk28, PBk29, PBk30, PBk31, PBk32, PBk33, PBk34, PBk35, NBk1, NBk2, NBk3, NBk4, NBk6; combinations thereof, and the like.

The pigments are milled to typically less than 1 micrometer, with a preferred particle size distribution of 10-500 nm. Preferably, the average particle size distribution is 10-350 nm, to have better transparency and a wide color gamut.

In order to incorporate the above-described pigments to the compositions, it is preferable that the pigments are manufactured and stably stored as a pigment concentrate in water. This is typically achieved by dispersing the pigment into a water-soluble or water-dispersible resin using a water-soluble and/or a water-dispersible surfactant which introduces hydrophilic functional groups into the surface of the pigment particles. Examples of these dispersing resins are numerous and could include polyvinyl alcohols, polyacrylic acid, acrylic acid-acrylonitrile copolymers, vinyl acetate-acrylate copolymers, acrylic acid-acrylate copolymers, styrene-acrylic acid copolymers, styrene-methacrylic acid copolymers, styrene-methacrylic acid-acrylate copolymers, styrene-alpha methyl styrene-acrylic acid copolymers, styrene-alpha methyl styrene-acrylic acid-acrylate copolymers, styrene-maleic acid copolymers, styrene-maleic anhydride copolymers, vinyl naphthalene-acrylic acid copolymers, vinyl naphthalene-maleic acid copolymers, vinyl acetate-maleate copolymers, vinyl acetate-crotonic acid copolymers, and vinyl acetate-acrylic acid copolymers, and the salts thereof. The copolymers can be used in any form of random copolymer, block copolymer, alternating copolymer and graft copolymer. Examples of such resins include Joncryl 67, 678, 8500, 586, 611, 680, 682, 683 and 69 available from BASF. Examples of the salts include sodium hydroxide, potassium hydroxide and salts of basic compounds such as ammonia, ethylamine, diethanolamine, triethanolamine, propylamine, isopropylamine, dipropylamine, butylamine, isobutyl amine, diethanolamine, triethanolamine, triisopropanolamine, dimethyl ethanolamine, amino methyl propanol, and morpholine. The amount of the basic compound is not strictly limited as long as the resin dispersant is equal to or more than the neutralization equivalent.

Examples of these surfactants used for the pigment dispersion include anionic surfactants such as alkane sulphonates, alpha-olefin sulphonates, alkyl benzene sulphonates, alkyl naphthalene sulphonates, acyl methyl taurinates, dialkyl sulfosuccinates, alkyl sulfates, sulfurized olefins, polyoxyethylene alkyl ether phosphates, polycarboxylic acids and mono glycerol phosphate, amphoteric surfactants such as alkylpyridinium salts and non-ionic surfactants such as polyoxyethylene alkyl ethers, polyoxyethylene alkyl phenyl ethers, polyoxyethylene alkyl esters, polyoxyethylene alkyl amides, glycerol alkyl esters and sorbitan alkyl esters. Examples include EFKA 1000, 4000, 5000 and 6000 series products from BASF, Tamol series products from Dow, and Solsperse 27,000, 40,000, 44,000, 46,000 and 47,000 from Lubrizol.

The curing of the inks of the present invention would preferably involve the use of UV light emitting diodes (LED) which are commercially available at a number of emission wavelengths (405, 395, 385, 375, 365 nm) with 395 nm or 385 nm being preferable. The use of a medium pressure mercury arc lamp is also a possibility but this strategy is not preferred because of the additional thermal load it places on the substrate in addition to that imparted by a drying regime to remove the water. Since there are many options known to the lamp manufacturers for reduction of heat transfer to the substrate, medium pressure mercury lamps cannot be ruled out. An additional lamp technology which may be useful for drying these inks is the low energy UV drying lamps sold by Colorific under the brand name "Light Bar". These Light Bar lamps also present minimal thermal load to the substrate.

EXAMPLES

The following examples illustrate specific aspects of the present invention and are not intended to limit the scope thereof in any respect and should not be so construed.

Synthesis of Photoinitiators of Formula I and IA

Examples 1 to 4 describe the synthesis of several photoinitiators of Formula I and IA. All $^1$H (proton) NMR were run on a Jeol ECX300 instrument at 300 MHz, 16 scans at 25° C. using deuterated DMSO (DMSO-d6) as solvent.

Example 1: Synthesis of 2-[carboxymethoxy]thioxanthone

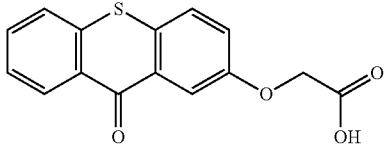 [SMILES: O=C(O)COc1ccc2sc3ccccc3c(=O)c2c1]

9.60 g (0.24 moles) of sodium hydroxide pellets and 80 ml of tetrahydrofuran were mixed in a 250 ml flask equipped with a stirrer, temperature probe and condenser. The mixture was heated to reflux for 5 minutes and then 9.21 g (0.0404 moles) of 2-hydroxy thioxanthone were added. The mixture was heated to reflux for 90 minutes. The mixture was cooled to 40° C. and 13.36 g (0.08 moles) of ethyl-2-bromoacetate were added and the mixture heated to reflux for 4 hours. The mixture was then cooled overnight. The mixture was then heated to reflux and 160 ml of deionised water was added. The tetrahydrofuran was distilled off and then the mixture was heated to reflux for 2 hours. The temperature was reduced to 95° C. and 16 ml of concentrated hydrochloric acid (10 M) was added slowly (10-15 minutes). The mixture was then heated to reflux for 10 minutes. After cooling to room temperature and stirring for 1 hour the mixture was filtered to collect the solid. The solid was washed with 3×40 ml of deionised water in the filter funnel and then dried in a vacuum oven at 80° C. for 8 hours to obtain the final product.

Yield 10.62 g (91.91%).
The product was analysed by NMR.
$^1$H NMR (300 MHz, DMSO-d6), δ 4.81 (2H, s), 7.38-8.38 (7H, m), 10.19 (1H, s).

Example 2: Synthesis of 2-[2-ethyl(carboxymethoxy)]thioxanthone

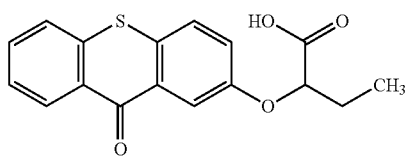 [SMILES: CCC(Oc1ccc2sc3ccccc3c(=O)c2c1)C(=O)O]

9.60 g (0.24 moles) of sodium hydroxide pellets and 80 ml of tetrahydrofuran were mixed in a 250 ml flask equipped with a stirrer, temperature probe and condenser. The mixture was heated to reflux for 5 minutes and then 9.21 g (0.0404 moles) of 2-hydroxy thioxanthone were added. The mixture was heated to reflux for 90 minutes. The mixture was cooled to 40° C. and 15.604 g (0.08 moles) of ethyl-2-bromobutyrate were added and the mixture heated to reflux for 4 hours. The mixture was then cooled overnight. The mixture was then heated to reflux and 160 ml of deionised water was added. The tetrahydrofuran was distilled off and then the mixture was heated to reflux for 2 hours. The temperature was reduced to 95° C. and 16 ml of concentrated hydrochloric acid (10 M) was added slowly (10-15 minutes). The mixture was then heated to reflux for 10 minutes. After cooling to room temperature and stirring for 1 hour the mixture was filtered to collect the solid. The solid was washed with 3×40 ml of deionised water in the filter funnel and then dried in a vacuum oven at 80° C. for 8 hours to obtain the final product.

Yield 11.57 g (92.11%).
The product was analysed by NMR.
$^1$H NMR (300 MHz, DMSO-d6), δ 1.03 (3H, t), 1.93 (2H, m), 4.82 (1H, t), 7.41-8.47 (7H, m), 10.19 (1H, s).

Example 3: Synthesis of 2-[2-methyl(carboxymethoxy)]thioxanthone

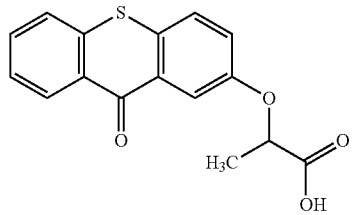 [SMILES: CC(Oc1ccc2sc3ccccc3c(=O)c2c1)C(=O)O]

9.60 g (0.24 moles) of sodium hydroxide pellets and 80 ml of tetrahydrofuran were mixed in a 250 ml flask equipped with a stirrer, temperature probe and condenser. The mixture was heated to reflux for 5 minutes and then 9.21 g (0.0404 moles) of 2-hydroxy thioxanthone were added. The mixture was heated to reflux for 90 minutes. The mixture was cooled to 40° C. and 14.484 g (0.08 moles) of ethyl-2-bromopropionate were added and the mixture heated to reflux for 4 hours. The mixture was then cooled overnight. The mixture was then heated to reflux and 160 ml of deionised water was added. The tetrahydrofuran was distilled off and then the mixture was heated to reflux for 2 hours. The temperature was reduced to 95° C. and 16 ml of concentrated hydrochloric acid (10 M) was added slowly (10-15 minutes). The mixture was then heated to reflux for 10 minutes. After cooling to room temperature and stirring for 1 hour the mixture was filtered to collect the solid. The solid was washed with 3×40 ml of deionised water in the filter funnel and then dried in a vacuum oven at 80° C. for 8 hours to obtain the final product.

Yield 10.90 g (90.8%).
The product was analysed by NMR.
$^1$H NMR (300 MHz, DMSO-d6), δ 1.55 (3H, 6), 4.98 (1H, q), 7.41-8.45 (7H, m), 10.19 (1H, s).

Example 4: Synthesis of 2-[carboxy-n-pentyl-5-oxy]thioxanthone

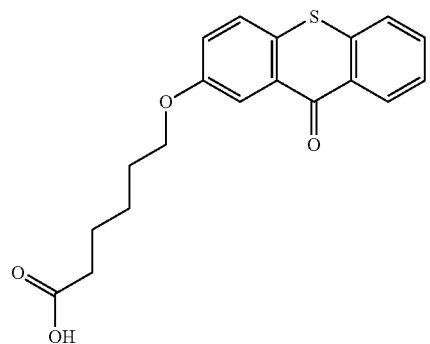 [SMILES: O=C(O)CCCCCOc1ccc2sc3ccccc3c(=O)c2c1]

9.60 g (0.24 moles) of sodium hydroxide pellets and 80 ml of tetrahydrofuran were mixed in a 250 ml flask equipped with a stirrer, temperature probe and condenser. The mixture was heated to reflux for 5 minutes and then 9.21 g (0.0404 moles) of 2-hydroxy thioxanthone were added. The mixture was heated to reflux for 90 minutes. The mixture was cooled to 40° C. and 17.849 g (0.08 moles) of ethyl-6-bromo-hexanoate were added and the mixture heated to reflux for 4 hours. The mixture was then cooled overnight. The mixture was then heated to reflux and 160 ml of deionised water was added. The tetrahydrofuran was distilled off and then the mixture was heated to reflux for 2 hours. The temperature was reduced to 95° C. and 16 ml of concentrated hydrochloric acid (10 M) was added slowly (10-15 minutes). The mixture was then heated to reflux for 10 minutes. After cooling to room temperature and stirring for 1 hour the mixture was filtered to collect the solid. The solid was washed with 3×40 ml of deionised water in the filter funnel and then dried in a vacuum oven at 80° C. for 8 hours to obtain the final product.

Yield 11.67 g (84.46%).

The product was analysed by NMR.

$^1$H NMR (300 MHz, DMSO-d6), δ 1.47-1.76 (8H, m), 2.25 (2H, t), 4.08 (2H, t), 7.3-8.48 (7H, m), 10.19 (1H, s).

Water-Based Energy Curable Inkjet Inks

Examples 5 to 16 describe water-based energy curable inkjet inks formulated with photoinitiators of Formula I and IA. All amounts of materials are in wt %.

Example 5: Cyan Water-Based Inkjet Inks 5A to 5C

Cyan water-based inkjet inks were prepared according to the formulations in Table 1. Inks 5A to 5C were formulated with CMTX as the photoinitiator. Comp. 1 is a comparative ink formulated with Irgacure 2959 as the photoinitiator.

The inks in Table 1 were printed onto a self-adhesive vinyl substrate using a 10 micron K bar from RK and dried using a hot air blower for 15 seconds to remove the solvent and giving a dry, tack-free film. This ink film was then cured using either a standard medium pressure mercury arc lamp at a dose of 235 mJ or an 8 Watts/cm$^2$ 395 nm LED lamp from Phoseon at a line speed of 27 m/min. The resistance of the cured ink was then assessed by a solvent rub test using a Satra STM421 rub tester with the pad soaked in deionised water. The test involves the rub tester moving the sample stage back and forth and the number of rubs recorded when the sample is showing multiple defects across the entire sample. Results are shown in Table 2 as an average of 2 runs.

TABLE 2

Water resistance test results of cyan water-based inkjet inks

| Example | Water rub resistance | |
|---|---|---|
| | LED Cure | UV Cure 235 mJ |
| Comp. 1 | 1 (No cure) | >200 |
| 5A | 89 | 172 |
| 5B | 112 | >200 |
| 5C | 200 | >200 |

The results in Table 2 demonstrate that the inks containing CMTX, a photoinitiator of Formula I and IA, have good utility using both LED and medium pressure mercury arc lamps. In addition, this utility is demonstrated at very low photoinitiator levels and relatively high amine levels. It is generally thought that a Type II photoinitiator such as CMTX would benefit from the use of an amine synergist, but typically this would be at a ratio of around 1:1 by weight with an amine synergist. In the present case, CMTX surprisingly shows significant benefit at an amine:CTMX ratio above 1:1, up to more than 20:1 for Example 5C.

Example 6: Cyan Water-Based Inkjet Inks 6A to 6C

Cyan inkjet inks were prepared according to the formulations in Table 3. Inks 6A to 6C were formulated with CMTX as the photoinitiator. Comp. 2 is a comparative ink formulated with Irgacure 2959 as the photoinitiator.

TABLE 1

Cyan water-based inkjet inks

| Material | Source/commercial code | Comp. 1 | 5A | 5B | 5C |
|---|---|---|---|---|---|
| UV crosslinkable aqueous polyurethane dispersion | Allnex, MS 10/1312 | 21 | 21 | 21 | 21 |
| Deionised water | | 45.9 | 46.6 | 45.41 | 44.22 |
| Solvent | Brenntag UK, Mono propylene glycol | 15 | 15 | 15 | 15 |
| Solvent | Univar, Butyl diglycol | 4 | 4 | 4 | 4 |
| Cyan pigment dispersion | Sun Chemical proprietary | 12.5 | 12.5 | 12.5 | 12.5 |
| Photoinitiator | Irgacure 2959, BASF | 1 | — | — | — |
| Photoinitiator | Carboxymethoxy thioxanthone, Great Lakes Chemical Company | — | 0.13 | 0.13 | 0.13 |
| Amine synergist | IMHOFF & STAHL GMBH, Triethanolamine | 0.2 | 0.37 | 1.56 | 2.75 |
| Biocide | CHEMLINK SPECIALITIES, Nipacide B1 | 0.1 | 0.1 | 0.1 | 0.1 |
| Surfactant | Alpha Chemicals, Capstone FS-3100 | 0.3 | 0.3 | 0.3 | 0.3 |
| Total | | 100.00 | 100.00 | 100.00 | 100.00 |

TABLE 3

Cyan water-based inkjet inks

| Material | Source/commercial code | Comp. 2 | 6A | 6B | 6C |
| --- | --- | --- | --- | --- | --- |
| UV crosslinkable aqueous polyurethane dispersion | Allnex, MS 10/1312 | 21 | 21 | 21 | 21 |
| Deionised water | | 45.9 | 44.44 | 43.88 | 43.1 |
| Solvent | Brenntag UK, Mono propylene glycol | 15 | 15 | 15 | 15 |
| Solvent | Univar, Butyl diglycol | 4 | 4 | 4 | 4 |
| Cyan pigment dispersion | Sun Chemical proprietary | 12.5 | 12.5 | 12.5 | 12.5 |
| Photoinitiator | Irgacure 2959, BASF | 1 | — | — | — |
| Photoinitiator | Carboxymethoxy thioxanthone, Great Lakes Chemical Company | — | 0.66 | 1.22 | 2.0 |
| Amine synergist | IMHOFF & STAHL GMBH, Triethanolamine | 0.2 | 2.0 | 2.0 | 2.0 |
| Biocide | CHEMLINK SPECIALITIES, Nipacide B1 | 0.1 | 0.1 | 0.1 | 0.1 |
| Surfactant | Alpha Chemicals, Capstone FS-3100 | 0.3 | 0.3 | 0.3 | 0.3 |
| Total | | 100.0 | 100.0 | 100.0 | 100.0 |

The inks in Table 3 were printed onto a self-adhesive vinyl substrate using a 10 micron K bar from RK and dried using a hot air blower for 15 seconds to remove all the solvent and giving a dry, tack-free film. This ink film was then cured using an 8 Watts/cm$^2$ 395 nm LED lamp from Phoseon at a line speed of 27 m/min. The resistance of the cured ink was then assessed by a solvent rub test using a Satra STM421 rub tester with the pad soaked in deionised water. The test involves the rub tester moving the sample stage back and forth and the number of rubs recorded when the sample is showing multiple defects across the entire sample. Results are shown in Table 4 as an average of 2 runs.

TABLE 4

Water resistance test results of cyan water-based inkjet inks

| Example | Water rub resistance |
| --- | --- |
| Comp. 2 | 1 (No cure) |
| 6A | >200 |
| 6B | 70 |
| 6C | 37 |

The results in Table 4 demonstrate that the Example 6A ink had good utility using LED, demonstrated at a photoinitiator level of 0.66%, but at higher photoinitiator levels (Examples 6B and 6C), where the ratio of photoinitiator to amine synergist is closer to 1:1, the reactivity falls markedly. This effect is in itself surprising as those skilled in the art would typically elect to use a Type II Photoinitiator such as CMTX at around 1:1 by weight with an amine synergist. However, while the reactivity of Examples 6B and 6C are inferior to Example 6A, 6B and 6C are still superior to the comparative example Comp 2, which has an α-hydroxy ketone as a photoinitiator, instead of thioxanthone.

Example 7: Magenta Water-Based Inkjet Inks 7A to 7J

Magenta inkjet inks were prepared according to the formulations in Table 5, with the polyurethane dispersions as shown in Table 6.

TABLE 5

Magenta water-based inkjet inks

| Material | Source/commercial code | % |
| --- | --- | --- |
| UV crosslinkable aqueous polyurethane dispersion | See Table 6 | 25.2 |
| Deionised water | | 43.7 |
| Solvent | Brenntag UK, Mono propylene glycol | 15 |
| Surface slip additive | TegoGlide 410, Evonik | 1 |
| Magenta pigment dispersion | Sun Chemical proprietary | 12.5 |
| Photoinitiator | Irgacure 2959 ex BASF | — |
| Photoinitiator | Carboxymethoxy thioxanthone, Great Lakes Chemical Company | 1.0 |
| Amine synergist | IMHOFF & STAHL GMBH, Triethanolamine | 1.2 |
| Biocide | CHEMLINK SPECIALITIES, Nipacide B1 | 0.1 |
| Surfactant | Alpha Chemicals, Capstone FS-3100 | 0.3 |
| Total | | 100.0 |

TABLE 6

Polyurethane Dispersions

| Example | Material | Source |
| --- | --- | --- |
| 7A | NeoRad R444 | DSM NeoResins |
| 7B | NeoRad R448 | DSM NeoResins |
| 7C | NeoRad UV14 40W | DSM NeoResins |
| 7D | NeoRad UV20 40W | DSM NeoResins |
| 7E | NeoRad UV-TN6711 40W | DSM NeoResins |
| 7F | NeoRad R441 | DSM NeoResins |
| 7G | NeoRad UV65 40W | DSM NeoResins |
| 7H | NeoRad R465 | DSM NeoResins |
| 7I | MS 10/1312 | Allnex |
| 7J | MS 10/1311 | Allnex |

The inks in Tables 5/6 were printed onto coated Lenetta charts (from Cornelius) using a 10 micron K bar from RK and dried using a hot air blower for 15 seconds to remove all the solvent and giving a dry, tack-free film. This ink film was then cured using an 8 Watts/cm² 395 nm LED lamp from Phoseon at line speeds of 25, 30, 50 and 70 m/min. The resistance of the cured ink was then assessed by a solvent rub test using a Satra STM421 rub tester with the pad soaked in deionised water. The test involves the rub tester moving the sample stage back and forth, and the number of rubs recorded when the sample is showing multiple defects across the entire sample. Results are shown in Table 7 as an average of 2 runs.

TABLE 7

Water resistance test results

| | Water rub resistance | | | |
|---|---|---|---|---|
| Example | 70 m/min | 50 m/min | 30 m/min | 25 m/min |
| 7A | 35 | 50 | 158 | >200 |
| 7B | 82 | >200 | >200 | — |
| 7C | 6 | 15 | 63 | 174 |
| 7D | 16 | 54 | >200 | >200 |
| 7E | 6 | 11 | 47 | 180 |
| 7F | 4 | 7 | 91 | 175 |
| 7G | 3 | 5 | 44 | 146 |
| 7H | 112 | >200 | >200 | — |
| 7I | 22 | 38 | 142 | >200 |
| 7J | 5 | 25 | >200 | >200 |

The results in Table 7 demonstrate that inks containing a variety of polyurethane dispersions have good utility using CMTX and being cured by LED. Some examples (7B and 7H) have notably higher reactivity and high resistance at the fastest line speeds, but all demonstrate good resistance properties and therefore good utility at 25 m/min.

Viscosities of inks 7A-7J were measured using the Brookfield DVII viscometer at 32° C. using a cup and bob accessory at a speed of 100 rpm. The results are given in Table 8.

TABLE 8

Viscosity test results

| Example | Viscosity (cPs at 32° C.) |
|---|---|
| 7A | 3.15 |
| 7B | 2.97 |
| 7C | 3.33 |
| 7D | 3.42 |
| 7E | 3.12 |
| 7F | 3.30 |
| 7G | 3.48 |
| 7H | 2.85 |
| 7I | 3.96 |
| 7J | Not recorded |

The results in Table 8 demonstrate that the inks containing CMTX and a variety of polyurethane dispersions demonstrate sufficiently low viscosity to have good utility in inkjet applications.

Example 8: Magenta Water-Based Inkjet Inks 8A to 8F

Magenta inkjet inks were prepared according to the formulations in Table 9.

TABLE 9

| Magenta water-based inkjet inks | | | | | | | |
|---|---|---|---|---|---|---|---|
| Material | Source/commercial code | 8A | 8B | 8C | 8D | 8E | 8F |
| UV crosslinkable aqueous polyurethane dispersion | MS 10/1312, Allnex | 25.2 | 25.2 | 25.2 | 25.2 | 25.2 | 25.2 |
| Deionised water | | 43.57 | 43.57 | 43.57 | 43.57 | 43.57 | 43.57 |
| Solvent | Brenntag UK, Mono propylene glycol | 15 | 15 | 15 | 15 | 15 | 15 |
| Surface slip additive | TegoGlide 410, Evonik | 1 | 1 | 1 | 1 | 1 | 1 |
| Magenta pigment dispersion | Sun Chemical proprietary | 12.5 | 12.5 | 12.5 | 12.5 | 12.5 | 12.5 |
| Photoinitiator | Carboxymethoxy thioxanthone, Great Lakes Chemical Company | 0.33 | 0.33 | 0.33 | 0.33 | 0.33 | 0.33 |
| Amine synergist | IMHOFF & STAHL GMBH, Triethanolamine | 2 | 1.8 | 1.6 | 1.4 | 1.2 | 1 |
| Amine synergist | N,N-dimethylamino benzoic acid | 0 | 0.2 | 0.4 | 0.6 | 0.8 | 1 |
| Biocide | CHEMLINK SPECIALITIES, Nipacide B1 | 0.1 | 0.1 | 0.1 | 0.1 | 0.1 | 0.1 |
| Surfactant | Alpha Chemicals, Capstone FS-3100 | 0.3 | 0.3 | 0.3 | 0.3 | 0.3 | 0.3 |
| Total | | 100 | 100 | 100 | 100 | 100 | 100 |
| pH of the ink at 25° C. | | 8.84 | 8.54 | 8.25 | 7.91 | 7.45 | 7.01 |

The inks in Table 9 were printed onto coated Lenetta charts (from Cornelius) using a 10 micron K bar from RK and dried using a hot air blower for 15 seconds to remove all the solvent and giving a dry, tack-free film. This ink film was then cured using an 8 Watts/cm² 395 nm LED lamp from Phoseon at a line speed of 40 m/min. The resistance of the cured ink was then assessed by a solvent rub test using a Satra STM421 rub tester with the pad soaked in deionised water. The test involves the rub tester moving the sample stage back and forth, and the number of rubs recorded when the sample is showing multiple defects across the entire sample. Results are shown in Table 10 as an average of 2 runs.

TABLE 10

Water resistance test results

| Example | Water rub resistance 40 m/min |
|---|---|
| 8A | 63 |
| 8B | 74 |
| 8C | 93 |
| 8D | 71 |
| 8E | 111 |
| 8F | 115 |

The results in Table 10 demonstrate that the inks containing a combination of the amine synergists triethanolamine and N,N-dimethylamino benzoic acid have good utility using CMTX and being cured by LED. The use of N,N-dimethylamino benzoic acid is in itself surprising, and has the dual benefit in the invention of allowing the pH rise associated with the use of high levels of an amine synergist such as triethanolamine to be mitigated and controlled to whatever pH range is desirable by balancing the level of the two materials. This is of value because, as will be known to those skilled in the art, highly basic solutions are both undesirable for the effective working of an inkjet head, and can lead to significant hydrolysis of some acrylate monomers causing long term stability issues. The results in Table 10 also indicate that N,N-dimethylamino benzoic acid is weight for weight a more effective amine synergist than triethanolamine.

Example 9: Black Water-Based Inkjet Inks 9A and 9B

Black inkjet inks were prepared according to the formulations in Table 11.

TABLE 11

Black water-based inkjet inks

| Material | Source/commercial code | 9A | 9B |
|---|---|---|---|
| UV crosslinkable aqueous polyurethane dispersion | MS 10/1312, Allnex | 20 | 20 |
| Deionised water | | 50.55 | 50.55 |
| Solvent | Brenntag UK, Mono propylene glycol | 14 | 14 |
| Surface slip additive | TegoGlide 410, Evonik | 1 | 1 |
| Black pigment dispersion | Sun Chemical proprietary | 12.5 | 12.5 |
| Amine synergist | 4-(N,N-dimethylamino) benzoic acid, Sigma-Aldrich | 0.1 | |
| Amine synergist | 3-(N,N-dimethylamino) benzoic acid ex Sigma-Aldrich | | 0.1 |
| Photoinitiator | Carboxymethoxy thioxanthone, Great Lakes Chemical Company | 0.62 | 0.62 |
| Amine synergist | IMHOFF & STAHL GMBH, Triethanolamine | 0.83 | 0.83 |
| Biocide | CHEMLINK SPECIALITIES, Nipacide B1 | 0.1 | 0.1 |
| Surfactant | Alpha Chemicals, Capstone FS-3100 | 0.3 | 0.3 |
| Total | | 100.0 | 100.0 |

The inks in Table 11 were printed onto coated Lenetta charts (from Cornelius) using a 10 micron K bar from RK and dried using a hot air blower for 15 seconds to remove all the solvent and giving a dry, tack-free film. This ink film was then cured using an 8 Watts/cm² 395 nm LED lamp from Phoseon, at line speeds of 20 and 30 m/min. The resistance of the cured ink was then assessed by a solvent rub test using a Satra STM421 rub tester with the pad soaked in deionised water. The test involves the rub tester moving the sample stage back and forth, and the number of rubs recorded when the sample is showing multiple defects across the entire sample. Results are shown in Table 12 as an average of 2 runs.

TABLE 12

Water resistance test results

| curing line speed | Water rub resistance | |
|---|---|---|
| | 9A | 9B |
| 20 m/min | 27 | 20 |
| 30 m/min | 9 | 9 |

The results in Table 12 demonstrate that a combination of the amine synergists triethanolamine and positional isomers of N,N-dimethylamino benzoic acid are capable of being used as effective amine synergists in water-based energy curable inkjet inks, and have good utility using CMTX, and being cured by LED.

Example 10: Magenta Water-Based Inkjet Inks 10A-10F

Magenta inkjet inks were prepared according to the formulations in Table 13.

TABLE 13

Magenta water-based inkjet inks

| Material | Source/commercial code | 10A | 10B | 10C | 10D | 10E | 10F |
|---|---|---|---|---|---|---|---|
| UV crosslinkable aqueous polyurethane dispersion | MS 10/1312, Allnex | 21 | 21 | 21 | 21 | 21 | 21 |
| Deionised water | | 45.6 | 45.6 | 45.6 | 45.6 | 45.6 | 45.6 |
| Solvent | Brenntag UK, Mono propylene glycol | 15 | 15 | 15 | 15 | 15 | 15 |
| Solvent | Butyl diglycol, Univar | 4 | 4 | 4 | 4 | 4 | 4 |
| Magenta pigment dispersion | Sun Chemical proprietary | 12.5 | 12.5 | 12.5 | 12.5 | 12.5 | 12.5 |
| Photoinitiator | Carboxymethoxy thioxanthone, Great Lakes Chemical Company | 0.5 | 0.5 | 0.5 | 0.5 | 0.5 | 0.5 |
| Amine synergist | IMHOFF & STAHL GMBH, Triethanolamine | 1 | | | | | |
| Amine synergist | N,N-dimethylethanolamine, Sigma-Aldrich | | 1 | | | | |
| Amine synergist | N-methyl diethanolamine, Sigma-Aldrich | | | 1 | | | |
| Amine synergist | CN386 aliphatic aminoacrylate, Sartomer | | | | 1 | | |
| Amine synergist | 3-dimethylaminopropan-1-ol, Sigma-Aldrich | | | | | 1 | |
| Amine synergist | 3-dimethylaminopropylacrylate, Sigma-Aldrich | | | | | | 1 |
| Biocide | CHEMLINK SPECIALITIES, Nipacide B1 | 0.1 | 0.1 | 0.1 | 0.1 | 0.1 | 0.1 |
| Surfactant | Alpha Chemicals, Capstone FS-3100 | 0.3 | 0.3 | 0.3 | 0.3 | 0.3 | 0.3 |
| Total | | 100.0 | 100.0 | 100.0 | 100.0 | 100.0 | 100.0 |

The inks in Table 13 were printed onto coated Lenetta charts (from Cornelius) using a 10 micron K bar from RK and dried using a hot air blower for 15 seconds to remove all the solvent and giving a dry, tack-free film. This ink film was then cured using an 8 Watts/cm$^2$ 395 nm LED lamp from Phoseon at line speeds of 30 and 40 m/min. The resistance of the cured ink was then assessed by a solvent rub test using a Satra STM421 rub tester with the pad soaked in deionised water. The test involves the rub tester moving the sample stage back and forth, and the number of rubs recorded when the sample is showing multiple defects across the entire sample. Results are shown in Table 14 as an average of 2 runs.

TABLE 14

Water resistance test results

| | Water rub resistance | |
|---|---|---|
| Example | 30 m/min | 40 m/min |
| 10A | >200 | 37 |
| 10B | 95 | 10 |
| 10C | >200 | 115 |
| 10D | >200 | >200 |
| 10E | 82 | 67 |
| 10F | 144 | 75 |

The results in Table 14 demonstrate that inks containing a range of different amine synergist structural types have good utility using CMTX and being cured by LED.

Example 11: Magenta Water-Based Inkjet Inks 11A-11E

Magenta inkjet inks were prepared according to the formulations in Table 15.

TABLE 15

Magenta water-based inkjet inks

| Material | Source/commercial code | 11A | 11B | 11C | 11D | 11E |
|---|---|---|---|---|---|---|
| UV crosslinkable aqueous polyurethane dispersion | NEORAD 444, DSM | 25.2 | 25.2 | 25.2 | 25.2 | 25.2 |
| Deionised water | | 43.7 | 43.7 | 43.7 | 43.7 | 43.7 |
| Solvent | Brenntag UK, Mono propylene glycol | 15 | 15 | 15 | 15 | 15 |

TABLE 15-continued

Magenta water-based inkjet inks

| Material | Source/commercial code | 11A | 11B | 11C | 11D | 11E |
|---|---|---|---|---|---|---|
| Surface slip additive | TegoGlide 410, Evonik | 1 | 1 | 1 | 1 | 1 |
| Magenta pigment dispersion | Sun Chemical proprietary | 12.5 | 12.5 | 12.5 | 12.5 | 12.5 |
| Amine synergist | IMHOFF & STAHL GMBH, Triethanolamine | 1.2 | 1.2 | 1.2 | 1.2 | 1.2 |
| Photoinitiator | Carboxymethoxy thioxanthone, Great Lakes Chemical Company | 1 | | | | |
| Photoinitiator | Example 1 | | 1 | | | |
| Photoinitiator | Example 2 | | | 1 | | |
| Photoinitiator | Example 3 | | | | 1 | |
| Photoinitiator | Example 4 | | | | | 1 |
| Biocide | CHEMLINK SPECIALITIES, Nipacide B1 | 0.1 | 0.1 | 0.1 | 0.1 | 0.1 |
| Surfactant | Alpha Chemicals, Capstone FS-3100 | 0.3 | 0.3 | 0.3 | 0.3 | 0.3 |
| Total | | 100.0 | 100.0 | 100.0 | 100.0 | 100.0 |
| | Viscosity at 32° C. | 3.03 | 3.12 | 3.15 | 3.06 | 3.18 |

The inks in Table 15 were printed onto coated Lenetta charts (from Cornelius) using a 10 micron K bar from RK and dried using a hot air blower for 15 seconds to remove all the solvent and giving a dry, tack-free film. This ink film was then cured using an 8 Watts/cm$^2$ 395 nm LED lamp from Phoseon at line speeds of 25, 30 and 50 m/min. The resistance of the cured ink was then assessed by a solvent rub test using a Satra STM421 rub tester with the pad soaked in deionised water. The test involves the rub tester moving the sample stage back and forth, and the number of rubs recorded when the sample is showing multiple defects across the entire sample. Results are shown in Table 16 as an average of 2 runs.

TABLE 16

Water resistance test results

| | Water rub resistance | | |
|---|---|---|---|
| Example | 25 m/min | 30 m/min | 50 m/min |
| 11A | 124 | 55 | 15 |
| 11B | 123 | 63 | 13 |
| 11C | >200 | 109 | 22 |

TABLE 16-continued

Water resistance test results

| | Water rub resistance | | |
|---|---|---|---|
| Example | 25 m/min | 30 m/min | 50 m/min |
| 11D | 164 | 106 | 25 |
| 11E | >200 | 168 | 42 |

The results in Table 16 demonstrate that inks containing a range of different thioxanthone structural types demonstrate good utility being cured by LED, with 11C & 11E in particular showing excellent reactivity. It should be noted that the inks containing a commercial form of CMTX (11A) and the laboratory synthesised version (11B) show virtually identical reactivity profiles.

Example 12: Yellow, Magenta, Cyan and Black Inkjet Inks 12A to 12D and 12E to 12H Yellow, magenta, cyan and black inkjet inks were prepared according to the formulations in Tables 17 and 18. Examples 12A to 12D were formulated using CMTX as the photoinitiator. Examples 12E to 12H (Comparative) were formulated using Irgacure 2959 as the photoinitiator.

TABLE 17

Yellow, magenta, cyan and black water-based inkjet inks 12A to 12D

| Material | Source/commercial code | 12A | 12B | 12C | 12D |
|---|---|---|---|---|---|
| UV crosslinkable aqueous polyurethane dispersion | MS 10/1312, Allnex | 20 | 25.2 | 21 | 20 |
| Deionised water | | 48.55 | 44.35 | 45.55 | 50.55 |
| Solvent | Brenntag UK, Mono propylene glycol | 12 | 15 | 15 | 14 |
| Solvent | Butyl diglycol, Univar | 4 | | 4 | |
| Yellow pigment dispersion | Dianippon ink and chemicals company (DIC) proprietary | 12.5 | | | |

TABLE 17-continued

Yellow, magenta, cyan and black water-based inkjet inks 12A to 12D

| Material | Source/commercial code | 12A | 12B | 12C | 12D |
|---|---|---|---|---|---|
| Magenta pigment dispersion | Sun Chemical proprietary | | 12.5 | | |
| Cyan pigment dispersion | Sun chemical proprietary | | | 12.5 | |
| Black pigment dispersion | Dianippon ink and chemicals company (DIC) proprietary | | | | 12.5 |
| Photoinitiator | Carboxymethoxy thioxanthone, IGM resins | 0.62 | 0.62 | 0.62 | 0.62 |
| Amine synergist | IMHOFF & STAHL GMBH, Triethanolamine | 0.83 | 0.83 | 0.83 | 0.83 |
| Amine synergist | N,N-dimethylamino benzoic acid, Sigma-Aldrich | 0.1 | 0.1 | 0.1 | 0.1 |
| Biocide | CHEMLINK SPECIALITIES, Nipacide B1 | 0.1 | 0.1 | 0.1 | 0.1 |
| Surface slip additive | TegoGlide 410, Evonik | 1 | 1 | 1 | 1 |
| Surfactant | Alpha Chemicals, Capstone FS-3100 | 0.3 | 0.3 | 0.3 | 0.3 |
| Total | | 100.0 | 100.0 | 100.0 | 100.0 |

TABLE 18

Yellow, magenta, cyan and black water-based inkjet inks 12E to 12H (Comparative)

| Material | Source/commercial code | 12E | 12F | 12G | 12H |
|---|---|---|---|---|---|
| UV crosslinkable aqueous polyurethane dispersion | MS 10/1312 ex Allnex | 20 | 25.2 | 21 | 20 |
| Deionised water | | 48.55 | 44.35 | 45.55 | 50.55 |
| Solvent | Brenntag UK, Mono propylene glycol | 12 | 15 | 15 | 14 |
| Solvent | Butyl diglycol, Univar | 4 | | 4 | |
| Yellow pigment dispersion | Dianippon ink and chemicals company (DIC) proprietary | 12.5 | | | |
| Magenta pigment dispersion | Sun Chemical proprietary | | 12.5 | | |
| Cyan pigment dispersion | Sun chemical proprietary | | | 12.5 | |
| Black pigment dispersion | Dianippon ink and chemicals company (DIC) proprietary | | | | 12.5 |
| Photoinitiator | Irgacure 2959 ex BASF | 0.62 | 0.62 | 0.62 | 0.62 |
| Amine synergist | IMHOFF & STAHL GMBH, Triethanolamine | 0.83 | 0.83 | 0.83 | 0.83 |
| Amine synergist | N,N-dimethylamino benzoic acid, Sigma-Aldrich | 0.1 | 0.1 | 0.1 | 0.1 |
| Biocide | CHEMLINK SPECIALITIES, Nipacide B1 | 0.1 | 0.1 | 0.1 | 0.1 |
| Surface slip additive | TegoGlide 410 ex Evonik | 1 | 1 | 1 | 1 |
| Surfactant | Alpha Chemicals, Capstone FS-3100 | 0.3 | 0.3 | 0.3 | 0.3 |
| Total | | 100.0 | 100.0 | 100.0 | 100.0 |

The inks in Table 17 and 18 were printed onto coated Lenetta charts (from Cornelius) using a 10 micron K bar from RK and dried using a hot air blower for 15 seconds to remove all the solvent and giving a dry, tack-free film. This ink film was then cured using either an 8 Watts/cm² 395 nm LED lamp from Phoseon at line speeds of 20 and 30 m/min, or at a dose of 145, 177 or 243 mJ under a medium pressure mercury arc lamp on a Primarc Maxicure UV rig. The resistance of the cured ink was then assessed by a solvent rub test using a Satra STM421 rub tester with the pad soaked in deionised water. The test involves the rub tester moving the sample stage back and forth, and the number of rubs recorded when the sample is showing multiple defects across the entire sample. Results are shown in Tables 19 and 20 as an average of 2 runs.

TABLE 19

Water resistance test results of inks 12A to 12D

| | | | Water rub resistance | | |
|---|---|---|---|---|---|
| Example | LED 30 m/min | LED 20 m/min | Medium Pressure Mercury 143 mJ | Medium Pressure Mercury 177 mJ | Medium Pressure Mercury 243 mJ |
| 12A | 64 | >200 | >200 | >200 | >200 |
| 12B | >200 | >200 | >200 | >200 | >200 |
| 12C | >200 | >200 | >200 | >200 | >200 |
| 12D | 63 | >200 | 85 | 172 | >200 |

TABLE 20

Water resistance test results of inks 12E to 12H (Comparative)

| | | | Water rub resistance | | |
|---|---|---|---|---|---|
| Example | LED 30 m/min | LED 20 m/min | Medium Pressure Mercury 143 mJ | Medium Pressure Mercury 177 mJ | Medium Pressure Mercury 243 mJ |
| 12E | No cure | No cure | >200 | >200 | >200 |
| 12F | No cure | No cure | >200 | >200 | >200 |
| 12G | No cure | No cure | >200 | >200 | >200 |
| 12H | No cure | No cure | >200 | >200 | >200 |

The results in Tables 19 and 20 demonstrate that the inks of different colours containing CMTX as the photoinitiator demonstrate good utility when cured by either an LED or a medium pressure mercury arc lamp. In contrast, the comparative examples containing the water soluble photoinitiator Irgacure 2959, well known to those skilled in the art as the preferred choice for water-based UV systems, show good cure using a medium pressure mercury arc lamp, but no cure at all using an LED lamp.

Examples 13 and 14: Black Inkjet Inks 13A to 13G and 14A to 14G

Black inkjet inks were prepared according to the formulations in Table 21 using each of 2 different acrylamides:
  Diacetone acrylamide (Sigma-Aldrich); giving formulations 13A to 13G
  N,N-methylene bisacrylamide (MRC Unitec); giving formulations 14A to 14G

TABLE 21

Black water-based inkjet inks

| Material | Source/commercial code | A | B | C | D | E | F | G |
|---|---|---|---|---|---|---|---|---|
| UV crosslinkable aqueous polyurethane dispersion | MS 10/1312 from Allnex | 20 | 20 | 20 | 20 | 20 | 20 | 20 |
| Deionised water | | 48.05 | 47.55 | 47.05 | 46.55 | 44.55 | 43.55 | 42.55 |
| Solvent | Brenntag UK, Mono propylene glycol | 12 | 12 | 12 | 12 | 12 | 12 | 12 |
| Solvent | Butyl diglycol, Univar | 4 | 4 | 4 | 4 | 4 | 4 | 4 |
| Surface slip additive | TegoGlide 410 from Evonik | 1 | 1 | 1 | 1 | 1 | 1 | 1 |
| Black pigment dispersion | Sun Chemical proprietary | 12.5 | 12.5 | 12.5 | 12.5 | 12.5 | 12.5 | 12.5 |
| Photoinitiator | Carboxymethoxy thioxanthone from Great Lakes Chemical Company | 0.62 | 0.62 | 0.62 | 0.62 | 0.62 | 0.62 | 0.62 |
| Amine synergist | IMHOFF & STAHL GMBH, Triethanolamine | 0.83 | 0.83 | 0.83 | 0.83 | 0.83 | 0.83 | 0.83 |
| Amine synergist | N,N-dimethylamino benzoic acid, Sigma-Aldrich | 0.1 | 0.1 | 0.1 | 0.1 | 0.1 | 0.1 | 0.1 |
| Acrylamide monomer | | 0.5 | 1 | 1.5 | 2 | 4 | 5 | 6 |
| Biocide | CHEMLINK SPECIALITIES, Nipacide B1 | 0.1 | 0.1 | 0.1 | 0.1 | 0.1 | 0.1 | 0.1 |
| Surfactant | Alpha Chemicals, Capstone FS-3100 | 0.3 | 0.3 | 0.3 | 0.3 | 0.3 | 0.3 | 0.3 |
| Total | | 100.0 | 100.0 | 100.0 | 100.0 | 100.0 | 100.0 | 100.0 |

The inks in Table 21 were printed onto coated Lenetta charts (from Cornelius) using a 10 micron K bar from RK and dried using a hot air blower for 15 seconds to remove all the solvent and giving a dry, tack-free film. This ink film was then cured using an 8 Watts/cm² 395 nm LED lamp from Phoseon at a line speed of 30 m/min. The resistance of the cured ink was then assessed by a solvent rub test using a Satra STM421 rub tester with the pad soaked in deionised water. The test involves the rub tester moving the sample stage back and forth, and the number of rubs recorded when the sample is showing multiple defects across the entire sample. Results are shown in Table 22 as an average of 2 runs.

The results in Table 22 demonstrate that inks containing 2 different acrylamide monomer types have good utility using CMTX and being cured by LED. In particular, 1-1.5% of N,N-methylene bisacrylamide and 5-6% diacetone acrylamide are particularly preferred.

Examples 15 and 16: Yellow Water-Based Inkjet Inks 15A to 15G and 16A to 16G

Yellow inkjet inks were prepared according to the formulations in Table 23 using each of 2 different acrylamides:

Diacetone acrylamide (Sigma-Aldrich); giving formulations 15A to 15G

N,N-methylene bisacrylamide (MRC Unitec); giving formulations 16A to 16G

TABLE 23

Yellow water-based inkjet inks

| Material | Source/commercial code | A | B | C | D | E | F | G |
|---|---|---|---|---|---|---|---|---|
| UV crosslinkable aqueous polyurethane dispersion | MS 10/1312 from Allnex | 20 | 20 | 20 | 20 | 20 | 20 | 20 |
| Deionised water | | 48.55 | 48.05 | 47.55 | 46.55 | 44.55 | 43.55 | 42.55 |
| Solvent | Brenntag UK, Mono propylene glycol | 12 | 12 | 12 | 12 | 12 | 12 | 12 |
| Solvent | Butyl diglycol, Univar | 4 | 4 | 4 | 4 | 4 | 4 | 4 |
| Surface slip additive | TegoGlide 410 from Evonik | 1 | 1 | 1 | 1 | 1 | 1 | 1 |
| Yellow pigment dispersion | Sun Chemical proprietary | 12.5 | 12.5 | 12.5 | 12.5 | 12.5 | 12.5 | 12.5 |
| Photoinitiator | Carboxymethoxy thioxanthone from Great Lakes Chemical Company | 0.62 | 0.62 | 0.62 | 0.62 | 0.62 | 0.62 | 0.62 |
| Amine synergist | IMHOFF & STAHL GMBH, Triethanolamine | 0.83 | 0.83 | 0.83 | 0.83 | 0.83 | 0.83 | 0.83 |
| Amine synergist | N,N-dimethylamino benzoic acid, Sigma-Aldrich | 0.1 | 0.1 | 0.1 | 0.1 | 0.1 | 0.1 | 0.1 |
| Acrylamide monomer | | 0 | 0.5 | 1 | 2 | 4 | 5 | 6 |
| Biocide | CHEMLINK SPECIALITIES, Nipacide B1 | 0.1 | 0.1 | 0.1 | 0.1 | 0.1 | 0.1 | 0.1 |
| Surfactant | Alpha Chemicals, Capstone FS-3100 | 0.3 | 0.3 | 0.3 | 0.3 | 0.3 | 0.3 | 0.3 |
| Total | | 100.0 | 100.0 | 100.0 | 100.0 | 100.0 | 100.0 | 100.0 |

TABLE 22

Water resistance test results

| | Acrylamide | Water rub resistance 30 m/min | |
|---|---|---|---|
| Example | monomer content (%) | 13 (Diacetone acrylamide) | 14 (N,N-methylene bisacrylamide) |
| A | 0.5 | 10 | 74 |
| B | 1 | 7 | 164 |
| C | 1.5 | — | 178 |
| D | 2 | 9 | 12 |
| E | 4 | 16 | 13 |
| F | 5 | 200 | — |
| G | 6 | 200 | 2 |

The inks in Table 23 were printed onto coated Lenetta charts (from Cornelius) using a 10 micron K bar from RK and dried using a hot air blower for 15 seconds to remove all the solvent and giving a dry, tack-free film. This ink film was then cured using an 8 Watts/cm² 395 nm LED lamp from Phoseon at a line speed of 30 m/min. The resistance of the cured ink was then assessed by a solvent rub test using a Satra STM421 rub tester with the pad soaked in deionised water. The test involves the rub tester moving the sample stage back and forth, and the number of rubs recorded when the sample is showing multiple defects across the entire sample. Results are shown in Table 24 as an average of 2 runs.

TABLE 24

Water resistance test results

| Example | Acrylamide monomer content (%) | Water rub resistance 30 m/min | |
| --- | --- | --- | --- |
| | | 15 (Diacetone acrylamide) | 16 (N,N-methylene bisacrylamide) |
| A | 0 | 16 | 16 |
| B | 0.5 | — | 46 |
| C | 1 | — | 71 |
| D | 2 | — | 33 |
| E | 4 | 22 | — |
| F | 5 | 99 | — |
| G | 6 | 71 | — |

The results in Table 24 demonstrate that inks containing two different acrylamide monomer types have good utility using CMTX and being cured by LED. In particular, 1-1.5% of N,N-methylene bisacrylamide and 5-6% diacetone acrylamide are particularly preferred, which mirrors the performance trends observed in the black inks for Examples 13 and 14.

The present invention has been described in detail, including the preferred embodiments thereof. However, it will be appreciated that those skilled in the art, upon consideration of the present disclosure, may make modifications and/or improvements on this invention that fall within the scope and spirit of the invention.

What is claimed is:

1. An alkaline energy curable water-based inkjet ink or coating composition comprising:
   a) a photoinitiator of Formula I:

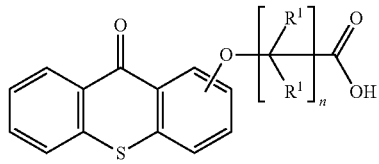

Formula I wherein each $R^1$ is an independently selected hydrogen or a $C_1$-$C_4$ alkyl group, and n is a number from 0 to 8;
   or a photoinitiator of Formula IA wherein Formula I is further substituted with $R^2$ and $R^3$,
   wherein each $R^2$ and $R^3$ is independently selected from the group consisting of hydrogen, $C_1$-$C_4$ alkyl, $C_1$-$C_4$ alkoxy, and halogen;
   y is 0 or 1;
   q is 0, 1, or 2;
   and n is a number from 0 to 8,
   and the photoinitiator has a structure of Formula IA:

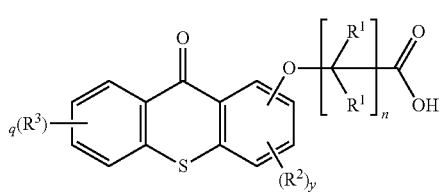

Formula IA b) a polymer which is water-soluble, or dispersible in water either as a liquid in liquid emulsion or a particle suspension;
   c) water; and
   d) one or more tertiary amine synergists;
   wherein the composition has a pH of between about 7.0 and about 9.5; and wherein the ratio of the amine synergists to the photoinitiator of Formula I or IA is greater than 1:1.

2. The alkaline energy curable water-based inkjet ink or coating composition of claim 1 comprising:
   a) the photoinitiator of Formula IA
   b) the polymer which is water-soluble, or dispersible in water, either as a liquid in liquid emulsion, or a particle suspension;
   c) water; and
   d) the one or more tertiary amine synergists;
   wherein the composition has a pH of between about 7.0 and about 9.5.

3. The composition of claim 1, which is curable by an LED light source.

4. The composition of claim 1, further containing one or more water compatible solvents, one or more water soluble monomers, and/or one or more additional photoinitiators.

5. The composition of claim 4, wherein:
   a) the photoinitiator of Formula I or IA is present in an amount of 0.1-2%;
   b) the polymer which is water-soluble, or dispersible in water either as a liquid in liquid emulsion or particle suspension is present in an amount of 15-35% of a water dispersion containing about 40% solids;
   c) water is present in an amount of 20-80%;
   d) the one or more tertiary amine synergists are present in an amount of 0.1-4%;
   e) the one or more water soluble monomers are present in an amount of 0-15%;
   f) the one or more water compatible solvents are present in an amount of 0-40%; and
   g) the one or more additional photoinitiators are present in an amount of 0-2%.

6. The composition of claim 1, wherein a ratio of amine to the photoinitiator of Formula 1 or Formula IA is greater than 1.5:1, greater than 2:1, greater than 5:1, greater than 10:1, greater than 15:1 or greater than 20:1.

7. The composition of claim 1, wherein the one or more tertiary amine synergists comprises at least one N,N-dialkylamino benzoic acid; and the composition further comprises at least one other tertiary amine synergist.

8. The composition of claim 1, further containing one or more additives selected from the group consisting of biocides, anti-mold additives, defoamers, de-aerators and surfactants and/or a colorant.

9. The composition of claim 1, wherein the photoinitiator of Formula I or Formula IA is selected from the group consisting of 2-[carboxymethoxy]thioxanthone, 2-[2-ethyl(carboxymethoxy)]thioxanthone, 2-[2-methyl(carboxymethoxy)]thioxanthone, and 2-[carboxy-n-pentyl-5-oxy]thioxanthone.

10. The composition of claim 1, wherein the polymer comprises an aqueous acrylated polyurethane dispersion.

11. The composition of claim 1, wherein the water is deionized.

12. A printed article comprising the composition of claim 1.

* * * * *